US012636494B2

(12) United States Patent
Kosunen et al.

(10) Patent No.: US 12,636,494 B2
(45) Date of Patent: May 26, 2026

(54) METHOD FOR CONTROLLING A STIMULATION SIGNAL AND A SYSTEM FOR PROVIDING A STIMULATION SIGNAL

(71) Applicant: Stichting IMEC Nederland, Eindhoven (NL)

(72) Inventors: Ilkka Kosunen, Utrecht (NL); Vojkan Mihajlovic, Eindhoven (NL)

(73) Assignee: STICHTING IMEC NEDERLAND, Eindhoven (NL)

( * ) Notice: Subject to any disclaimer, the term of this patent is extended or adjusted under 35 U.S.C. 154(b) by 643 days.

(21) Appl. No.: 18/074,831

(22) Filed: Dec. 5, 2022

(65) Prior Publication Data

US 2023/0181902 A1     Jun. 15, 2023

(30) Foreign Application Priority Data

Dec. 10, 2021    (EP) ..................................... 21213779

(51) Int. Cl.
*A61N 1/36*          (2006.01)

(52) U.S. Cl.
CPC ................................ *A61N 1/36034* (2017.08)

(58) Field of Classification Search
CPC .............. A61N 1/36034; A61N 1/0529; A61N 1/36139; A61N 1/0476; A61N 1/36031; A61N 1/0456; A61B 5/37; A61B 5/374; A61B 5/383; A61B 5/4836
USPC ......................................................... 607/59
See application file for complete search history.

(56) References Cited

U.S. PATENT DOCUMENTS

| | | | |
|---|---|---|---|
| 2014/0257016 A1* | 9/2014 | Ahmed | A61N 2/02 |
| | | | 607/48 |
| 2016/0008632 A1 | 1/2016 | Wetmore | |
| 2016/0074663 A1* | 3/2016 | De Ridder | A61N 1/36192 |
| | | | 607/59 |
| 2017/0157398 A1* | 6/2017 | Wong | A61B 5/6824 |
| 2017/0333711 A1 | 11/2017 | Tass et al. | |

(Continued)

FOREIGN PATENT DOCUMENTS

| | | | |
|---|---|---|---|
| EP | 3517159 A1 | 7/2019 | |
| WO | WO-2013192582 A1 * | 12/2013 | A61B 5/055 |

OTHER PUBLICATIONS

Karabanov et al: "Transcranial brain stimulation: closing the loop between brain and stimulation", Current Opinion in Neurology, vol. 29, No. 4, pp. 397-404, 2016.

(Continued)

*Primary Examiner* — Carl H Layno
*Assistant Examiner* — Mary Grace Schlueter
(74) *Attorney, Agent, or Firm* — MOSER TABOADA

(57) ABSTRACT

A method for controlling a stimulation signal for brain stimulation comprises: transmitting a trigger signal for triggering a stimulation generator to output a high frequency synchronization signal exhibiting periodical modifications; receiving a measurement signal representing brain activity comprising neural oscillations and a response to the high frequency synchronization signal; determining adjustment of a phase of the stimulation signal based on a phase difference between the neural oscillations and the modifications of the high frequency synchronization signal; and transmitting a phase information signal for providing information of an adjusted phase of the stimulation signal to be used by the stimulation generator.

15 Claims, 7 Drawing Sheets

(56) References Cited

U.S. PATENT DOCUMENTS

| | | |
|---|---|---|
| 2017/0340855 A1 | 11/2017 | Soulet De Brugiere et al. |
| 2018/0133507 A1 | 5/2018 | Malchano et al. |
| 2018/0169373 A1 | 6/2018 | Tass et al. |
| 2018/0264264 A1 | 9/2018 | Skorheim et al. |
| 2019/0021657 A1 | 1/2019 | Mohammadrezazadeh et al. |
| 2019/0134395 A1 * | 5/2019 | Fitzgerald .......... A61N 1/36031 |
| 2019/0336070 A1 | 11/2019 | Youm et al. |
| 2020/0139113 A1 * | 5/2020 | Shin ..................... A61N 1/0476 |
| 2021/0023369 A1 | 1/2021 | Jeong et al. |

OTHER PUBLICATIONS

Bergmann et al: "Brain State-Dependent Brain Stimulation", Frontiers in Psychology, vol. 9, Article 2108, pp. 1-4, 2018.

Bergmann et al: "Combining non-invasive transcranial brain stimulation with neuroimaging and electrophysiology: Current approaches and future perspectives", NeuroImage, vol. 140, pp. 4-19, 2016.

Thut et al: "Guiding transcranial brain stimulation by EEG/MEG to interact with ongoing brain activity and associated functions: A position paper", Clinical Neurophysiology, vol. 128, No. 5, pp. 843-857, 2017.

Lerner et al: "Transcranial Current Stimulation During Sleep Facilitates Insight into Temporal Rules, but does not Consolidate Memories of Individual Sequential Experiences", Nature Scientific Reports, 9:1516, pp. 1-17, 2019.

Raco et al: "Combining TMS and tACS for Closed-Loop Phase-Dependent Modulation of Corticospinal Excitability: A Feasibility Study", Frontiers in Cellular Neuroscience, vol. 10, Article 143, pp. 1-8, 2016.

Extended European Search Report in EP21213779.8 dated May 25, 2022.

* cited by examiner

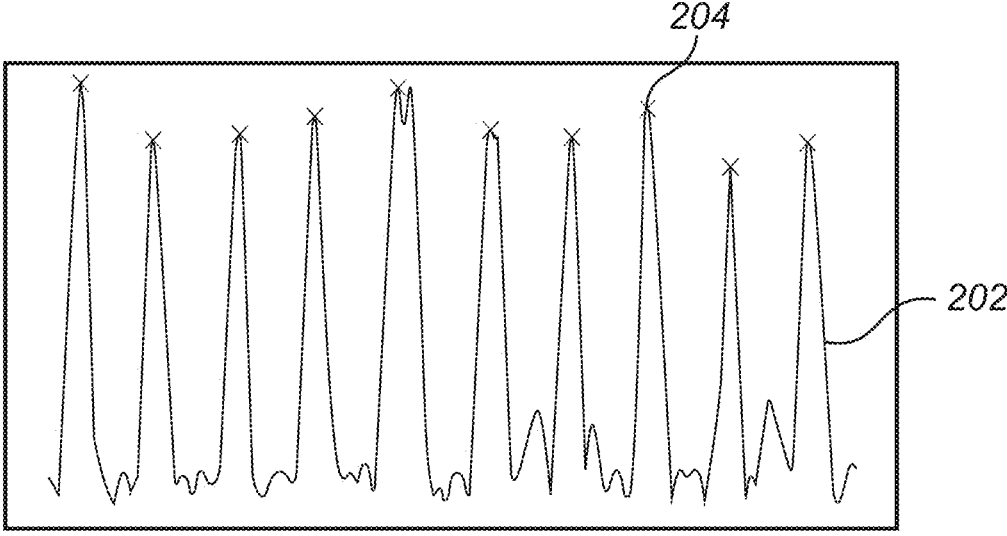
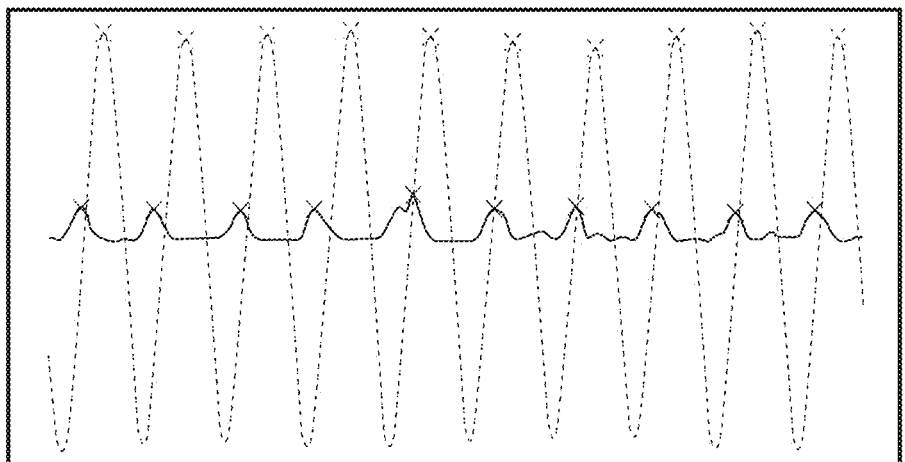
*Fig. 4*

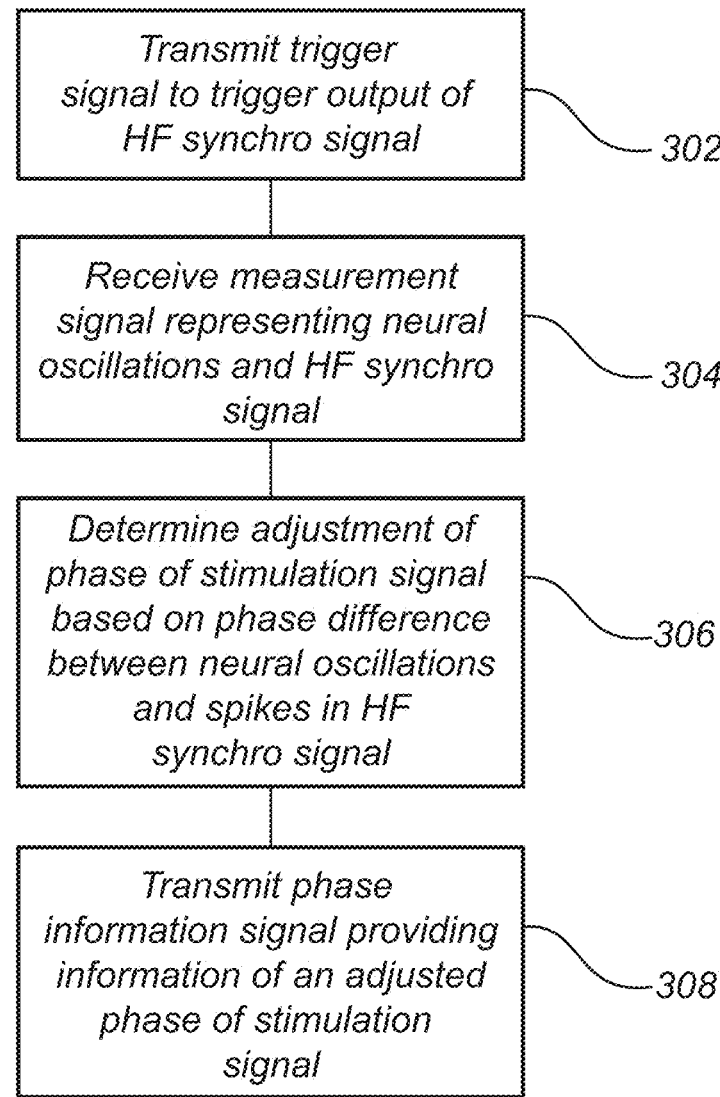

Transmit trigger
signal to trigger output of
HF synchro signal — 302

Receive measurement
signal representing neural
oscillations and HF synchro
signal — 304

Determine adjustment of
phase of stimulation signal
based on phase difference
between neural oscillations
and spikes in HF
synchro signal — 306

Transmit phase
information signal providing
information of an adjusted
phase of stimulation
signal — 308

*Fig. 5*

METHOD FOR CONTROLLING A STIMULATION SIGNAL AND A SYSTEM FOR PROVIDING A STIMULATION SIGNAL

CROSS-REFERENCE TO RELATED APPLICATION

The present application claims the benefit of and priority to EP Patent Application Serial No. 21213779.8, filed Dec. 10, 2021, the entire contents of which is incorporated herein by reference.

TECHNICAL FIELD

The present inventive concept relates to a method for controlling a stimulation signal and a system for providing a stimulation signal. In particular, the stimulation signal may be used for brain stimulation.

BACKGROUND

The central nervous system exhibits neural oscillations in form of rhythmic or repetitive patterns of neural activity. A large number of neurons can have a synchronized neural activity giving rise to macroscopic oscillations. The macroscopic oscillations may be referred to as brain waves.

Different types of brain waves having different frequencies may be detected. Thus, brain waves may be referred to as delta waves (0.5-3 Hz), theta waves (3-8 Hz), alpha waves (8-12 Hz), beta waves (12-38 Hz) and gamma waves (38-42 Hz). However, it should be realized that the exact frequency range of the respective types of waves is not well-established. The brain waves may be detected using electroencephalography (EEG).

The effect of the brain waves is not entirely known, but the brain waves have been shown to be strongly associated with mental states. For example, alpha waves have been shown to increase during relaxation and may be associated with a mood of a subject. The brain waves may also be related to memory functions and cognitive performance.

Transcranial alternating current stimulation (tACS) is a method that could be used for strengthening desired neural oscillations in the brain or for suppressing undesired neural oscillations. In particular, a tACS signal may interfere with a brain wave signal in the brain to cause constructive or destructive interference, so as to strengthen desired neural oscillations or suppress undesired neural oscillations, respectively. It may be desired to strengthen neural oscillations for increasing relaxation of the subject, or for improving cognitive performance of the subject. On the other hand, it may be desired to suppress neural oscillations that have a detrimental effect, such as high frequency neural oscillations (>80 Hz) having even a higher frequency than gamma waves that may be associated with epileptic seizures.

Interference of two signals with similar frequency is dependent on relation of phase of the signals to each other. Hence, in order to control interference of the tACS signal with the brain wave signal, phase of the tACS signal should be controlled. However, in order to obtain a desired phase relation between the signals, a high temporal accuracy of control of the tACS signal is required. Achieving high temporal accuracy, in range of milliseconds, may be very difficult using a tACS device, because the tACS device may have multiple sources of delay (that may be varying), such as delays for generating a command to start stimulation/ adapt phase of the stimulation signal and delays for executing the command. Further, brain wave activity may also be dynamic such that a phase offset of the brain wave signal may change over time. This implies that synchronization of the stimulation signal to a desired phase relation may be needed to be periodically updated.

Therefore, it is difficult to obtain a desired phase relation between a stimulation signal and a brain wave signal.

SUMMARY

An objective of the present inventive concept is to provide a robust control of phase relation between a stimulation signal and a brain wave signal. It is a particular objective of the present inventive concept to provide a control of the phase relation which is agnostic to a signal path for providing a trigger signal for triggering and/or adjusting a stimulation signal.

These and other objectives of the present inventive concept are at least partly met by the invention as defined in the independent claims. Preferred embodiments are set out in the dependent claims.

According to a first aspect, there is provided a method for controlling a stimulation signal for brain stimulation, said method comprising: transmit a trigger signal for triggering a stimulation generator to output a high frequency synchronization signal exhibiting periodical modifications; receive a measurement signal representing brain activity comprising neural oscillations and a response to the high frequency synchronization signal; determine adjustment of a phase of the stimulation signal based on a phase difference between the neural oscillations and the modifications of the high frequency synchronization signal; and transmit a phase information signal for providing information of an adjusted phase of the stimulation signal to be used by the stimulation generator.

According to the inventive concept, the high frequency synchronization signal is used for determining phase information to be used for the stimulation signal. The same stimulation generator will be used for outputting both the high frequency synchronization signal and the stimulation signal. This implies that the phase relation or synchronization between the high frequency synchronization signal and the stimulation signal can be accurately controlled.

The high frequency synchronization signal comprises periodical modifications of the signal, wherein the modifications have high frequency content. This implies that the high frequency content of the modifications may be easily extracted from a measurement signal, which may include brain activity content and the high frequency content. However, by the high frequency synchronization signal having periodical modifications, a periodicity of the modifications may be related to the neural oscillations. The periodicity may be set to relate to a frequency of interest in the neural oscillations. This implies that a timing of the modifications within the high frequency synchronization signal may be related to the neural oscillations. This timing may be used for ensuring that the stimulation signal has a desired phase relationship to the neural oscillations.

Hence, adjustment of the phase of the stimulation signal may be performed to ensure that a desired phase relation of the stimulation signal to the neural oscillations is set based on a phase of the neural oscillations at an instant corresponding to a modification of the high frequency synchronization signal. Thus, there may be said to be a phase difference between the neural oscillations and the instant of the modification of the high frequency synchronization signal.

Once a phase relation between the neural oscillations and the modifications of the high frequency synchronization signal is known, a phase of the stimulation signal may be accurately set in relation to the neural oscillations. Since the same stimulation generator is used for outputting the high frequency synchronization signal and the stimulation signal, the phase of the stimulation signal may be set in relation to the high frequency synchronization signal. Accuracy of the phase of the stimulation signal is independent of how long a delay is between providing a trigger for output of the stimulation signal and the stimulation signal being output, because the stimulation generator knows how to relate the stimulation signal to the high frequency synchronization signal having a known timing of the modifications. In particular, the accuracy of the phase of the stimulation signal is independent of any variations in the delay.

It is not necessary to determine an exact delay between the neural oscillations and the modifications of the high frequency synchronization signal, i.e. it is not necessary to keep track of which of the modifications that is being compared to the neural oscillations. Rather, it is sufficient to determine the phase relation between the neural oscillations and any of the modifications of the high frequency synchronization signal. This phase relation enables accurate control of the stimulation signal in relation to the neural oscillations. Hence, it is possible to ignore all sources of noises and delays from wireless connections or software and operating systems involved in control of generation of the stimulation signal. By setting the phase of the stimulation signal in relation to the modifications of the high frequency synchronization signal, a desired phase relation to the neural oscillations may be achieved.

The use of a high frequency synchronization signal implies that the synchronization signal will not cause significant effect on brain activity of the subject. Hence, the high frequency synchronization signal may be output to allow the stimulation signal to be accurately controlled in relation to the neural oscillations while the subject is not affected, or insignificantly affected, by the output of the high frequency synchronization signal.

The method for controlling the stimulation signal may be performed during a control interval while output of the stimulation signal is temporarily interrupted, or in preparation of output of the stimulation signal. Thus, it should be realized that the phase information signal may adjust a phase of a stimulation signal so that a phase of the stimulation signal is changed (or maintained the same) in relation to a temporarily interrupted stimulation signal. Also, the phase information signal may adjust or set a phase of the stimulation signal, such as adjusting the phase in relation to a default relation to the high frequency synchronization signal, before the stimulation signal is output when preparing for output of the stimulation signal.

A duration of each modification in the high frequency synchronization signal may be so short that the instant corresponding to the modification of the high frequency synchronization signal is well-defined. In this regard, the duration of the modification may be short in relation to a period of the frequency of interest of the neural oscillations, such as duration being less than 20% of the period of the frequency of interest of the neural oscillations. For instance, the duration may be a few ms, such as about or shorter than 10 ms. It should further be realized that the instant corresponding to the modification of the high frequency synchronization signal may be determined as a particular feature of the modification, the instant of which may be determined in a well-defined manner. For instance, the instant corresponding to the modification of the high frequency synchronization signal may be determined as an onset of the modification, an end of the modification or a peak of the modification. This implies that the phase relation of the neural oscillations to the high frequency synchronization signal may be very accurately determined.

A modification of the high frequency synchronization signal should be interpreted as any signal feature of the high frequency synchronization signal that can be provided in a periodical manner and which differentiates from signal around the modification such that the modification may be identified in the signal. The modification may be a spike or pulse being provided with a well-defined periodical interval between subsequent spikes or pulses. Thus, the spike or pulse may have a high frequency content, whereas the high frequency synchronization signal may be zero or have a constant level between the spikes or pulses.

However, it should be realized that the modification of the high frequency synchronization signal may be a modulation of the high frequency synchronization signal. Thus, amplitude modulations may be provided in a periodical manner, such that a (much) higher amplitude of the high frequency synchronization signal is provided at instants corresponding to the modifications. Thus, a constant frequency may be output by the high frequency synchronization signal, but with modulations of the amplitude.

It should be realized that the high frequency synchronization signal has a frequency which is "high" at least in respect to the frequency of the synchronization signal being larger than the stimulation signal. In embodiments, the frequency of the synchronization signal may be at least 5 times, such as at least 10 times, such as at least 100 times larger than the frequency of the stimulation signal. This implies that the high frequency synchronization signal should be easily extracted from the measurement signal, in that the high frequency synchronization signal differs from a frequency of interest in the neural oscillations (which frequency is at least similar to the frequency of the stimulation signal). It should be realized that the frequency of the synchronization signal may be selected in relation to the frequency content of the neural oscillations, such that the frequency of the synchronization signal may be set to be at least 50 Hz, such as at least 100 Hz. Such frequencies may differentiate the high frequency synchronization signal from normal frequency content of the neural oscillations. However, it should be realized that in some situations, a subject may exhibit higher frequency oscillations in the brain activity, such as in case of epileptic seizures. Thus, if the method is to be used for subjects which may exhibit higher frequency oscillations in the brain activity, a higher frequency of the synchronization signal may be selected in order to ensure that the high frequency synchronization signal may be reliably extracted from the measurement signal. For instance, the frequency of the high frequency synchronization signal may be set to at least 1 kHz, or even larger. Further, it should be realized that the frequency of the synchronization signal may be set to be at least 1 kHz or even larger, regardless whether the subject exhibits higher frequency oscillations in the brain activity.

The modifications being periodical implies that there is a repetition in the high frequency synchronization signal with a well-defined period. Thus, the period at which the modifications are repeated differs from the frequency content of the high frequency synchronization signal. Rather, the period at which the modifications are repeated should be related to the frequency of interest of the neural oscillations with which the stimulation signal is to interfere. Thus, the period at which the modifications are repeated could be the same as the period associated with the frequency of interest of the neural oscillations, or the periods could have a well-defined relation to each other, such as being related by one or more integer factors.

The measurement signal representing brain activity comprising neural oscillations implies that the measurement signal comprises signals that correspond to electrical activity in the brain. The electrical activity may be measured by electroencephalography (EEG). The measurement signal representing brain activity may thus be recorded using EEG electrodes that may be attached on scalp of the subject. However, it should be realized that a measurement signal representing brain activity may alternatively be recorded using electrodes placed directly on an exposed surface of the brain, so called intracranial EEG (iEEG) or electrocorticography (ECoG). According to another alternative, the measurement signal representing brain activity may be recorded by electrodes that may be implanted or inserted into the brain, such as electrodes of a neural probe. Hence, that the measurement signal represents brain activity that is recorded using electrodes arranged in any manner for direct recording of electrical activity in the brain.

The measurement signal representing a response to the high frequency synchronization signal implies that the measurement signal comprises signal content based on the high frequency synchronization signal being output. The high frequency synchronization signal may be output into the brain through at least one pair of electrodes. The measurement signal may be detected using a different pair of electrodes, such that the response corresponds to the high frequency synchronization signal propagating through brain tissue or any other tissue between the pairs of electrodes. The measurement signal may even be acquired using the same pair of electrodes for stimulation and for measurement.

The measurement signal represents both brain activity and the response to the high frequency synchronization signal such that a combined signal is recorded, which may later be separated to represent the neural oscillations and the high frequency synchronization signal separately.

The neural oscillations may comprise signal content over a range of frequencies. Thus, a frequency of interest may be selected among the neural oscillations, such that the phase difference between the neural oscillations and the modifications is determined for the frequency of interest. This frequency of interest should have a well-defined relation to the period of the modifications. However, it should be realized that the period of the modifications may be changed in order to allow the stimulation signal to be controlled in relation to another frequency of interest.

The frequency of interest may relate to a typical frequency of a brain wave of the subject. The method may be used for controlling the stimulation signal in relation to any type of brain waves, such as delta waves, theta waves, alpha waves, beta waves or gamma waves. In embodiments, the method may be used for controlling a stimulation signal in relation to alpha waves, which may be useful in increasing relaxation of the subject. However, it should be realized that the stimulation signal may be controlled in relation to other types of brain waves and that control may be changed between different types of brain waves.

It should be realized that the stimulation signal may be controlled in order to provide a constructive interference between the stimulation signal and the neural oscillations. This may be useful in promoting desired brain waves or other desired neural oscillations. However, it should further be realized that the stimulation signal may alternatively be controlled in order to provide a destructive interference between the stimulation signal and the neural oscillations. This may be useful in suppressing undesired brain waves or other undesired neural oscillations.

The phase information signal may be set such that the stimulation signal may be synchronized with the neural oscillations, such that a constructive interference is achieved. The phase information signal may alternatively be set such that the stimulation signal may be set to a phase offset of 180° to the neural oscillations, such that a destructive interference is achieved. It should however be realized that the phase information signal may be set in any manner for achieving any phase relation between the stimulation signal and the neural oscillations.

The phase information signal may be used for controlling a timing of the modifications of the high frequency synchronization signal. For instance, the modifications may be set to coincide with start of a period of the neural oscillations (phase=0°), but it should be realized that any other phase relation may be set. Then, the stimulation signal may be set to always use a constant phase relation to the instants of the modifications of the high frequency synchronization signal. In this manner, the phase of the stimulation signal may be controlled by setting a timing of the modifications of the high frequency synchronization signal. However, it should be realized that the phase information signal may alternatively be used for setting a desired phase relation between the stimulation signal and the instants of the modifications of the high frequency synchronization signal.

The stimulation generator may continuously output the high frequency synchronization signal, such that the high frequency synchronization signal is output during output of the stimulation signal. Since the high frequency synchronization signal may not affect the brain of the subject, the high frequency synchronization signal may be continuously output without harming the subject. Since the phase of the stimulation signal may be determined in relation to the instants of modifications of the high frequency synchronization signal, it may be easier to provide a reliable control of the stimulation signal if the high frequency synchronization signal is continuously output. However, it should be realized that output of the high frequency synchronization signal may be terminated when the phase offset of the stimulation signal to be used has been determined.

It should be realized that the method for controlling the stimulation signal may be performed in any control unit, which is able to provide control signals for controlling the stimulation generator. Thus, the method does not involve steps for outputting the stimulation signal, but rather only involves the steps for controlling the stimulation signal to be output. This control may be provided by a control unit within the stimulation generator but may equally well be provided by a separate control unit. Similarly, the method does not involve actual steps for acquiring the measurement signal. Rather, the measurement signal may be separately acquired and may then be transmitted to the control unit that controls the stimulation signal such that the measurement signal may be received therein. Hence, the method relates to an ingenious manner of processing signals to achieve a desired phase relation between signals, which processing may be used for controlling a stimulation signal for brain stimulation. However, the method does not relate to output or any control of effects of the output of the stimulation signal.

According to an embodiment, the method further comprises updating adjustment of a phase of the stimulation signal, wherein said updating comprises: transmit a pause signal for pausing the stimulation generator from outputting the stimulation signal; receive an updated measurement signal representing the brain activity comprising neural oscillations and the response to the high frequency synchronization signal; determine an updated adjustment of a phase of the stimulation signal based on the phase difference between the neural oscillations and the modifications of the high frequency synchronization signal; and transmit an updated phase information signal for providing information of an updated adjusted phase of the stimulation signal to be used by the stimulation generator.

The control of the stimulation signal may be performed at regular control intervals so as to update the phase of the stimulation signal. This implies that the stimulation signal may be controlled in order to adapt to any changes in the neural oscillations.

It should be realized that the neural oscillations may change over time, such that the phase relation may drift over time and a desired interference of the stimulation signal with the neural oscillations may not be maintained unless the stimulation signal is controlled to adjust the phase regularly.

For instance, updating of the phase of the stimulation signal may be performed every five minutes to ensure that a desired relation between the stimulation signal and the neural oscillations may be maintained.

Since the stimulation signal has a similar or identical frequency to the frequency of interest of the neural oscillations, the stimulation signal may need to be paused during the control intervals, so as to allow the neural oscillations to be properly detected in the updated measurement signal. As an alternative, an amplitude control signal may be provided for controlling the stimulation generator to lower the amplitude of the stimulation signal during the control interval. Thus, output of the stimulation signal need not be completely paused during the control interval but instead the stimulation signal may be set to such a low amplitude that the stimulation signal will not interfere with detecting the neural oscillations in the measurement signal.

According to an embodiment, a time window between the pause signal and the updated phase information signal is less than 10 seconds, such as less than 3 seconds.

Hence, a time window of the control interval may be relatively short. This implies that the updated adjustment of a phase of the stimulation signal may be quickly determined to allow the stimulation signal to again be output after the adjustment of the phase.

The time window still allows averaging of the phase relation over a large number of waves of the neural oscillations, such that a robust determination of the phase difference between the neural oscillations and the modifications of the high frequency synchronization signal may be determined. It should be realized that using a relatively long time window, such as 10 seconds or longer, the control intervals form a relatively large portion of an overall time used for providing stimulations. However, if a relatively short time window is used, such as an approximately 1 second long time window, the phase difference may not be accurately determined.

According to an embodiment, the stimulation generator is controlled to output the high frequency synchronization signal with a lower amplitude than the stimulation signal.

The frequency of the high frequency synchronization signal will typically not interfere with frequency content of the brain activity. This implies that the high frequency synchronization signal may be accurately identified, even if the amplitude of the high frequency synchronization signal is low.

Hence, the amplitude of the high frequency synchronization signal may be controlled to be lower than the amplitude of the stimulation signal, such as lower than 50% of the amplitude of the stimulation signal.

Using a high frequency synchronization signal with a low amplitude may further ensure that the high frequency synchronization signal will not affect the brain of the subject or that the high frequency synchronization signal affects any other nearby equipment.

According to an embodiment, the stimulation generator is triggered to output the high frequency synchronization signal with periodical modifications, wherein a periodicity of the modifications is an integer number of a frequency of the neural oscillations.

Thus, the modifications will be provided with a periodicity that relates to the frequency of interest in the neural oscillations. This implies that a phase of the neural oscillations at an instant corresponding to a modification of the high frequency synchronization signal will be the same at different instants corresponding to different modifications, because the time period between these modifications will correspond to one or more full periods of the neural oscillations.

It should be realized that the integer number may be larger than 1. This implies that a plurality of modifications may be provided at each period of the neural oscillations. This may allow a larger number of data points to be used for determining a phase relation between the neural oscillations and the modifications of the high frequency synchronization signal. However, the method may need to keep track of the modifications within a period of the neural oscillations to ensure that the stimulation signal may be controlled to a desired phase relation to the neural oscillations.

This may also allow the stimulation signal being controlled in relation to one of a plurality of modifications within the period corresponding to a single wave of the neural oscillation. This implies that the phase of the stimulation signal may be controlled by selecting which of the modifications in each period of the neural oscillations that the stimulation signal is to be synchronized with and/or by performing only a slight adjustment of the phase of the stimulation signal in relation to one of the modifications. This may improve accuracy of control of the phase of the stimulation signal.

However, the integer number may according to an alternative be 1. In such case, the phase of the neural oscillations at an instant corresponding to a modification of the high frequency synchronization signal will be the same at all different instants corresponding to different modifications, allowing the phase difference between the neural oscillations and the modifications to be easily determined.

According to an embodiment, the method further comprises receiving an initial calibration measurement signal representing the brain activity comprising neural oscillations, determining a personalized frequency of the neural oscillations, and controlling the stimulation generator to output the high frequency synchronization signal with the periodicity of the modifications being an integer number of the personalized frequency of the neural oscillations.

This implies that the control of the stimulation signal may be adapted to subject-specific neural oscillations. For instance, a peak frequency within a desired frequency range may be determined, such as determining a frequency having a peak amplitude among alpha waves of the subject.

The determining of the personalized frequency may correspond to determining a peak frequency, such as a peak frequency among alpha waves. Then, the stimulation signal may be used for promoting or suppressing the peak frequency of the neural oscillations. However, it should be realized that the personalized frequency may be determined to be off the peak frequency, or the personalized frequency may be determined based on any other feature in the initial calibration measurement signal, such as a frequency with a lowest amplitude or a center frequency in a range of frequencies having an amplitude above a threshold.

Calibration may also be performed intermittently, such that the personalized frequency may be updated, or a check may be performed to determine whether an update of the personalized frequency would be desired.

According to an embodiment, determining adjustment of the phase of the stimulation signal comprises determining a phase of the neural oscillations using a wavelet or Hilbert transform.

The measurement signal may represent brain activity comprising a plurality of frequencies of the neural oscillations. Thus, processing of the measurement signal is needed in order to determine the phase of the neural oscillations of the frequency of interest.

Using a wavelet transform or a Hilbert transform, determination of the phase of the neural oscillations is enabled.

According to an embodiment, determining adjustment of the phase of the stimulation signal comprises determining a timing of the modifications of the high frequency synchronization signal based on detecting a peak amplitude of the modifications.

The phase of the neural oscillations is to be compared to timing of the modifications in order for the phase difference to be determined. Hence, the timing of the modifications, or instant at which the modifications occur, may need to be determined. The peak amplitude of the modifications may be used as an indicator of the timing of the modifications. This may be suitable since the timing of the peak amplitude may be relatively easy to determine. However, it should be realized that another feature of the modifications may be used as an indicator of the timing of the modifications, such as a peak or valley, or change of sign of a derivative of the high frequency synchronization signal.

According to a second aspect, there is provided a control unit for controlling a stimulation signal for brain stimulation, wherein the control unit is configured to perform the method according to the first aspect.

Effects and features of this second aspect are largely analogous to those described above in connection with the first aspect. Embodiments mentioned in relation to the first aspect are largely compatible with the second aspect.

The control unit allows control of the stimulation signal for brain stimulation such that the stimulation signal may be accurately controlled in a simple manner for ensuring that the stimulation signal has a desired phase relation to a frequency of interest of neural oscillations.

The control unit may be implemented as a general-purpose processing unit, such as a central processing unit (CPU), which may execute instructions of one or more computer programs in order to implement functionality of the control unit. However, the control unit may alternatively be implemented as firmware arranged e.g. in an embedded system, or as a specifically designed processing unit, such as an Application-Specific Integrated Circuit (ASIC) or a Field-Programmable Gate Array (FPGA).

According to a third aspect, there is provided a computer program product comprising computer-readable instructions such that when executed on a processing unit the computer-readable instructions will cause the processing unit to perform the method according to the first aspect.

Effects and features of this third aspect are largely analogous to those described above in connection with the first, and second aspects. Embodiments mentioned in relation to the first, and second aspects are largely compatible with the third aspect.

The computer program product may thus provide computer-readable instructions for allowing the method to be implemented. This allows the functionality of the method to be provided to any processing unit.

The computer program product may comprise a non-transient computer-readable medium for carrying the computer-readable instructions. Alternatively, the computer program product may comprise a signal carrying the computer-readable instructions, e.g. for communicating the computer program product to the processing unit through wired or wireless communication.

According to a fourth aspect, there is provided a system for providing a stimulation signal for brain stimulation, wherein the system comprises: the control unit according to the second aspect, and a stimulation generator, which is configured to receive the trigger signal and the phase information signal from the control unit and is configured to generate and output the high frequency synchronization signal exhibiting periodical modifications and the stimulation signal.

Effects and features of this fourth aspect are largely analogous to those described above in connection with the first, second, and third aspects. Embodiments mentioned in relation to the first, second, and third aspects are largely compatible with the fourth aspect.

Thus, the system unit allows control and output of the stimulation signal for brain stimulation such that the stimulation signal may be accurately controlled in a simple manner for ensuring that the stimulation signal has a desired phase relation to a frequency of interest of neural oscillations.

The control unit may be arranged within a common housing with the stimulation generator, such that the control unit may communicate internally within the housing with the stimulation generator.

In addition, a measurement unit for recording the measurement signal may also be arranged within the common housing. Thus, the system may be self-contained within the common housing providing a compact system for brain stimulation.

However, it should be realized that the control unit and the stimulation generator may be separately arranged in different units. The stimulation generator may preferably be arranged relatively close to the subject which is to receive the stimulation signals in order to ensure integrity of the stimulation signals being provided to electrodes connected to the subject. However, the control unit may be arranged in any unit, remote from the stimulation generator. Thus, the control unit may be arranged in a separate computer, which may be arranged in the same room as the stimulation generator and the control unit and the stimulation generator may be configured to communicate over a direct wired or wireless communication.

According to an alternative, the control unit may be arranged in a completely different location from the stimulation generator. The control unit and the stimulation generator may then be configured to communicate through wired or wireless communication over a computer network, such as a local area network. According to yet another alternative, the control unit may be arranged anywhere, and the control unit and the stimulation generator may be configured to communicate over any computer or telecommunication network, such as the Internet. For example, the control unit may be arranged "in the cloud".

According to an embodiment, the stimulation generator is configured to provide a synchronized output of the stimulation signal with the periodical modifications of the high frequency synchronization signal, and wherein the stimulation generator is configured to adjust a timing of the periodical modifications for adjusting the phase of the stimulation signal.

Thus, the stimulation signal may always be set with a constant phase relation between the stimulation signal and the instants of the modifications of the high frequency synchronization signal. Thus, onset of a period (phase=0°) may be synchronized with an instant of the modifications. This implies that the high frequency synchronization signal may be adjusted in order to adjust timing of the periodical modifications based on the phase information signal. Once this adjustment of the high frequency synchronization signal is achieved, the stimulation signal may be automatically adjusted to the desired phase relation using the constant relation between the phase of the stimulation signal and the timing of the periodical modifications.

This may be a simple manner of controlling the stimulation signal. The control of the stimulation signal may also be robust since the stimulation signal uses a constant relation to the high frequency synchronization signal.

However, it should be realized that the phase of the stimulation signal may be adjusted in different manners, such as by changing a phase offset of the stimulation signal in relation to the timing of the modifications of the high frequency synchronization signal.

According to an embodiment, the stimulation generator is configured to output the stimulation signal to provide transcranial alternating current stimulation (tACS).

The system for providing brain stimulation may be suitable for use with tACS, which is an established method for providing brain stimulation.

According to an embodiment, the system further comprises a plurality of stimulation electrodes for providing a plurality of stimulation signals to the brain through the plurality of stimulation electrodes.

This implies that the system may be used for localized stimulation at a plurality of brain regions. The stimulation signals at different locations may be synchronized or set to a desired phase relation. Phase of each stimulation signal may be individually controlled in relation to locally determined phase of the local neural oscillations or phase of each stimulation signal may be jointly controlled in relation to a combination of phases (e.g. mean phase) of the neural oscillations at locally recorded neural oscillations. Different frequencies and phase relations may be used at different locations, which may be used for strengthening or weakening network interaction within the brain.

Hence, it should be realized that the system may be used in a vast number of ways using a plurality of stimulation signals being provided to a plurality of stimulation electrodes.

According to an embodiment, the system is configured to control a relative phase and/or a relative frequency of the plurality of stimulation signals.

This implies that the system is configured to control the stimulation signals in relation to each other. The system may comprise a plurality of stimulation generators, each associated with different stimulation electrodes for outputting the plurality of stimulation signals. However, the stimulation generators may all need to be connected to a common synchronization generator for ensuring that a desired relative phase of the stimulation signals may be achieved.

BRIEF DESCRIPTION OF THE DRAWINGS

The above, as well as additional objects, features, and advantages of the present inventive concept, will be better understood through the following illustrative and non-limiting detailed description, with reference to the appended drawings. In the drawings like reference numerals will be used for like elements unless stated otherwise.

FIG. 4 shows graphs illustrating determination of timing of modifications of the synchronization signal and illustrating phase difference between neural oscillations in the brain activity signal and timing of the modifications of the synchronization signal.

FIG. 5 is a flow chart of a method according to an embodiment.

DETAILED DESCRIPTION

Figure 1:
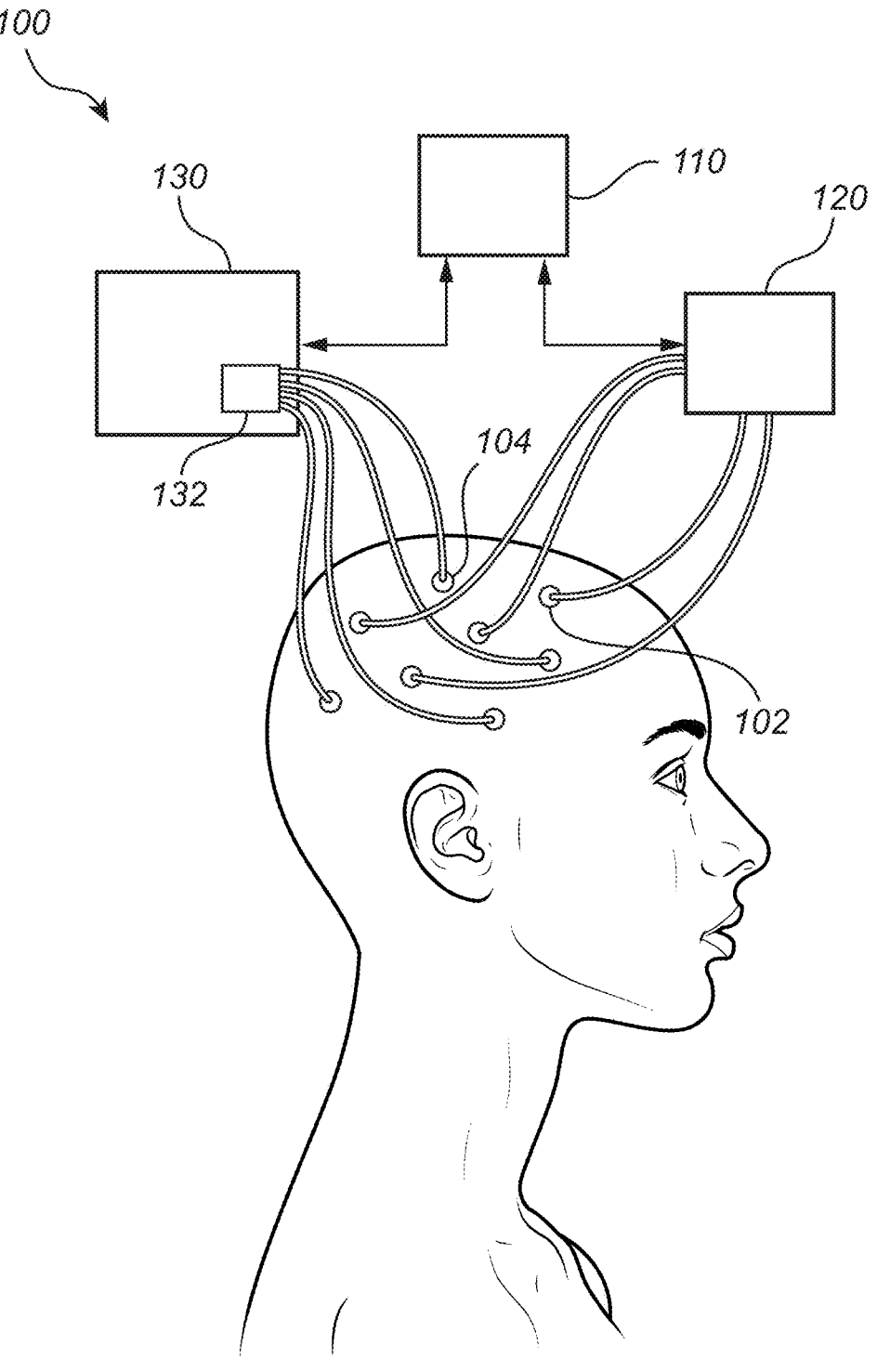
FIG. 1 is a schematic view of a system according to an embodiment.

Referring now to FIG. 1, a system 100 for providing a stimulation signal for brain stimulation will be described. The system 100 comprises a control unit 110 for controlling the stimulation signal and a stimulation generator 120 configured to generate and output the stimulation signal.

As shown in FIG. 1, the system 100 may be set up to provide a transcranial stimulation, such as transcranial alternating current stimulation (tACS). Thus, the system 100 may comprise stimulation electrodes 102, which may be configured to be attached to a scalp of a subject such that the stimulation signal may be provided to the brain of the subject through the cranium. However, it should be realized that the system 100 may alternatively be set up to provide stimulation signals in another manner to the brain, such as using electrodes that may be attached to an exposed brain corresponding to a set-up for recording an electrocorticography (ECoG) signal, or using electrodes in a neural probe that is to be inserted into brain tissue.

The system 100 may comprise a measurement unit 130 for measuring brain activity. The measurement unit 130 may comprise sensing electrodes 104 configured to record electrical signals in the brain so as to record electrical activity in the brain. The measurement unit 130 may comprise sensing electrodes 104 for electroencephalography (EEG) recording, ECoG recording or for otherwise recording electrical activity in the brain.

The sensing electrodes 104 of the measurement unit 130 may be connected to a signal processing unit 132 of the measurement unit 130 for acquiring a measurement signal based on the electrical potentials at the sensing electrodes 104.

Electrical activity in the brain may involve neural oscillations in form of rhythmic or repetitive patterns of neural activity. A large number of neurons can have a synchronized neural activity giving rise to macroscopic oscillations. The macroscopic oscillations may be referred to as brain waves.

Different types of brain waves having different frequencies may be detected. Thus, brain waves may be referred to as delta waves (0.5-3 Hz), theta waves (3-8 Hz), alpha waves (8-12 Hz), beta waves (12-38 Hz) and gamma waves (38-42 Hz).

The measurement unit 130 may be configured to acquire a measurement signal which may represent brain waves in the brain of the subject. The measurement unit 130 may be configured to acquire a measurement signal which encompasses a frequency range which includes the frequencies of the different types of brain waves.

The stimulation electrodes 102 and the sensing electrodes 104 may be arranged close to each other, such that measurement of electrical activity in the brain may occur close to a location where stimulation is provided. In fact, electrodes may be used both for stimulation and for sensing, such that electrodes may be connected both to the stimulation generator 120 for providing a stimulation signal and to the signal processing unit 132 of the measurement unit 130 for acquisition of the measurement signal. However, the stimulation electrodes 102 and the sensing electrodes 104 need not necessarily be arranged close to each other.

The stimulation generator 120 is configured to output a high frequency synchronization (HF synchro) signal which is to be used for determining a phase of a stimulation signal in relation to neural oscillations of the brain activity.

The HF synchro signal comprises high frequency content, which has a frequency higher than the stimulation signal. The high frequency content may be provided as periodically occurring modifications in the HF synchro signal. Thus, the HF synchro signal may be constant, such as having a constant zero amplitude, between the periodical modifications and the HF synchro signal may further comprise periodical spikes or pulses which form the high frequency content of the HF synchro signal. The periodical spikes or pulses may correspond to a pulse train, such as a few periods of a high frequency wave. At least a major part of power of the periodical spikes or pulses may be in a high frequency.

According to an alternative, the HF synchro signal comprises a high frequency signal, which is provided with periodically occurring modifications in form of changes of the amplitude of the HF synchro signal such that the amplitude is periodically increased for a short period of time.

The high frequency content of the HF synchro signal has at least a higher frequency than a stimulation signal used for providing brain stimulation. The high frequency content of the HF synchro signal may have a frequency larger than typical brain waves, such as having a frequency of at least 50 Hz, such as at least 100 Hz.

A frequency of the HF synchro signal may be selected such that the frequency may be easily detected in a measurement signal of electrical activity in the brain, i.e. there should be a low level of signal content in the brain at the frequency. This implies that an amplitude of the modifications in the HF synchro signal may be low, while still allowing the modifications to be reliably detected. For instance, the amplitude of the modifications of the HS synchro signal may be lower than an amplitude of the stimulation signal.

Further, the frequency of the HF synchro signal may be selected such that the frequency will not affect or will minimally affect the brain, such that the subject is not affected by the use of the HF synchro signal.

The periodicity of the modifications is set to correspond to a frequency of interest for which brain stimulation is to be provided. Thus, instants at which modifications occur in the HF synchro signal may be related to the neural oscillations in the brain, such that the HF synchro signal may be used for determining a phase relation and allowing a stimulation signal to be provided with an accurate phase relation to the neural oscillations in the brain, as will be explained in further detail below.

The stimulation generator 120 may be any type of unit which is able to controllably output an electrical signal. The stimulation generator 120 may be configured to tune parameters of the output electrical signal so as to control the output electrical signal. For instance, the stimulation generator 120 may be configured to tune frequency, phase, and waveform of the electrical signal. The stimulation generator 120 may further be configured to generate the electrical signal using selected parameters. The stimulation generator 120 may be connected to the stimulation electrodes 102 and output the generated electrical signal to stimulation electrodes 102.

The stimulation generator 120 is configured to generate and output the HF synchro signal to the stimulation electrodes 102. The stimulation generator is further configured to generate and output the stimulation signal to the stimulation electrodes 102.

When the stimulation generator 120 outputs the HF synchro signal, the measurement unit 130 may acquire a measurement signal which may represent brain activity comprising neural oscillations and further represent a response to the HF synchro signal. Thus, the output of the HF synchro signal at the stimulation electrodes 102 implies that the HF synchro signal will also be detected in the measurement signal. The response to the HF synchro signal may simply be that the HF synchro signal has propagated from the stimulation electrodes 102 to the sensing electrodes 104 so as to be detected by the sensing electrodes 104.

The control unit 110 is configured to receive the measurement signal from the measurement unit 130. The control unit 110 may further use the periodical modifications in the HF synchro signal so as to determine a phase relation between the neural oscillations in the measurement signal and instants of the modifications. This phase relation may be used in order to determine an adjustment of a phase of the stimulation signal such that the stimulation signal may be provided with a desired phase relation to the neural oscillations, as will be described in further detail below.

The control unit 110 is further configured to transmit a phase information signal to the stimulation generator 120 such that the stimulation generator 120 may use information of an adjustment of the phase of the stimulation signal to control output of the stimulation signal by the stimulation generator 120.

Thus, the system 100 allows an adjustment of the phase of the stimulation signal to be based on the relation between the modifications of the HF synchro signal and the neural oscillations. The phase of the stimulation signal may further be reliably set in relation to the instants of the modifications of the HF synchro signal. Thus, the stimulation generator 120 may reliably provide a desired phase relation of the stimulation signal to the neural oscillations.

Since the stimulation generator 120 adjusts the phase in relation to the known timing of the modifications of the HF synchro signal, it does not matter how long a command to adjust a phase is delayed before it is executed. This implies that the control of the stimulation signal is agnostic to a signal path used for sending commands for adjusting the phase. Further, it ensures that the stimulation signal may be reliably output with a desired phase in a simple manner using simple circuitry.

Further, it should be realized that it does not matter how far away the stimulation electrodes 102 are from sensing electrodes 104. The sensing electrodes 104 sense the relation to the HF synchro signal to the neural oscillations at the sensing electrodes 104 based on the HF synchro signal being output by the stimulation electrodes 102. When the stimulation signal is also output by the stimulation electrodes 102 with a phase set in relation to the HF synchro signal, it will imply that the desired phase of the stimulation signal in relation to the neural oscillations will also be achieved.

The control unit 110 may be configured to control functions of all components in the system 100. The control unit 110 may be configured to provide control signals for initiating actions to be taken in the system 100.

Thus, the control unit 110 may be configured to transmit a trigger signal to the stimulation generator 120 for triggering the stimulation generator 120 to initially output the HF synchro signal. Once a phase to be used for the stimulation signal has been determined, the control unit 110 may further transmit a trigger signal to the stimulation generator 120 for triggering the stimulation generator 120 to output the stimulation signal using the desired phase.

The control unit 110, the stimulation generator 120 and the measurement unit 130 may all be arranged in a common housing. The measurement unit 130 may comprise circuitry for acquiring the measurement signal and possibly (pre-) processing the measurement signal, such as providing analog-to-digital conversion of the measurement signal. The stimulation generator 120 may also comprise circuitry for generating an electrical signal based on input parameters.

The control unit 110 may be implemented in a general-purpose processing unit, such as a central processing unit (CPU), which may execute instructions of one or more computer programs in order to implement functionality of the control unit 110. However, the control unit 110 may alternatively be implemented as firmware arranged e.g. in an embedded system, or as a specifically designed processing unit, such as an Application-Specific Integrated Circuit (ASIC) or a Field-Programmable Gate Array (FPGA).

Thus, the control unit 110, the stimulation generator 120 and the measurement unit 130 may be implemented as separate units within the common housing and may be configured to communicate by transmitting signals between the units within the housing. However, it should be realized that functions of the control unit 110, the stimulation generator 120 and the measurement unit 130 may even be intertwined, such that parts of the stimulation generator 120 and the measurement unit 130 may also be implemented in a common processing unit with the control unit 110 so that the different units may be defined by different threads within the common processing unit.

Further, it should be realized that the control unit 110, the stimulation generator 120 and the measurement unit 130 may be arranged in separate physical housings. Whereas the stimulation generator 120 and the measurement unit 130 may need to be arranged in close relation to the subject, the control unit 110 may be remotely arranged. The control unit 110, the stimulation generator 120 and the measurement unit 130 may then be configured to communicate through wired or wireless communication over a computer and/or telecommunication network.

Figure 2:
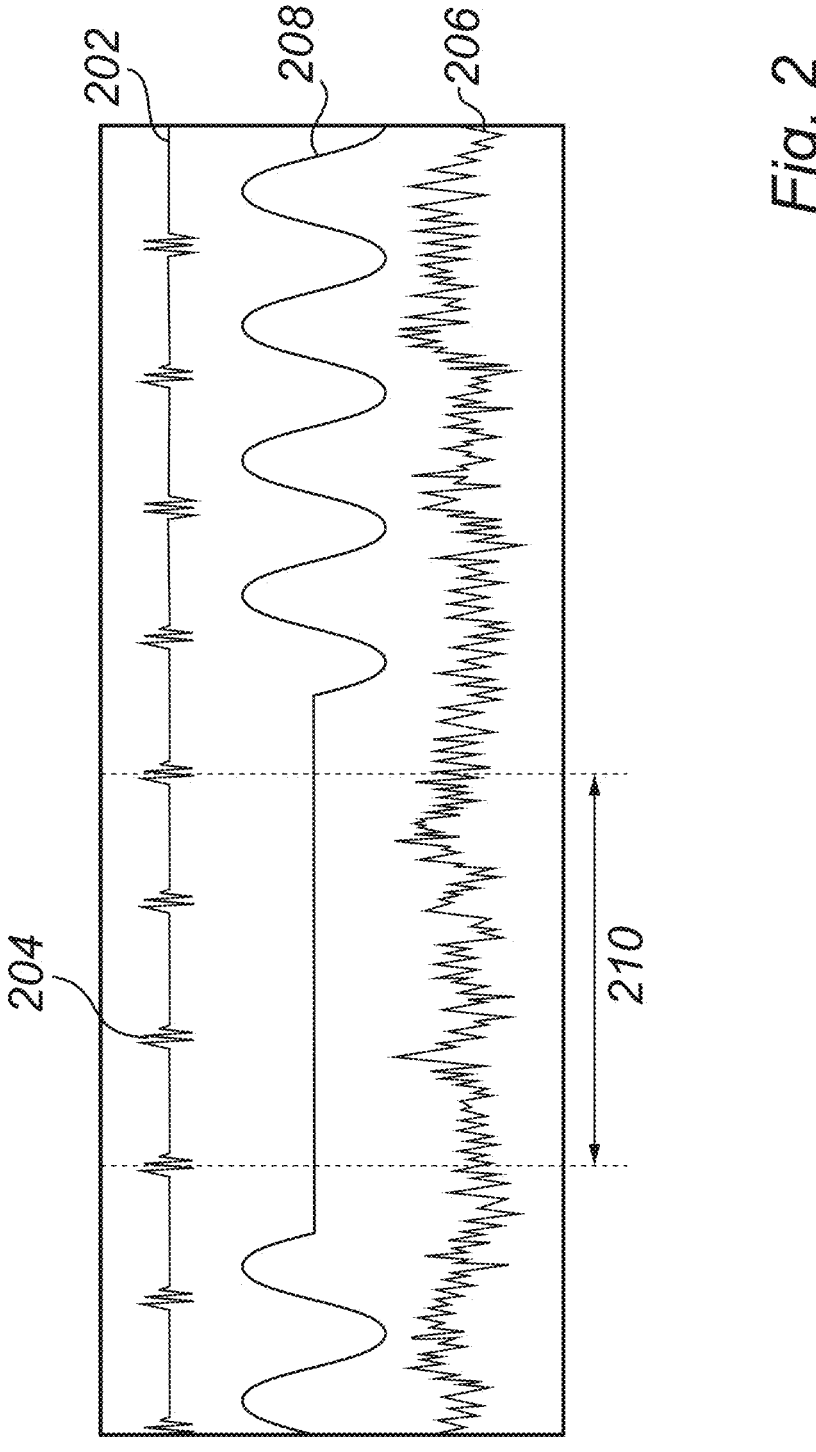
FIG. 2 is a schematic view of a synchronization signal, a stimulation signal, and a brain activity signal.

Referring now to FIG. 2, control of phase of the stimulation signal will be described in further detail.

FIG. 2 illustrates a HF synchro signal 202 which is non-zero only at periodical modifications in form of spikes 204. The instants at which the spikes 204 are provided are provided with a period corresponding to a frequency of interest of the neural oscillations. The period may be adjusted in order to fit different frequencies of interest of the neural oscillations.

Below, the periodical modifications will be referred to as spikes 204, but it should be realized that other modifications of the HF synchro signal 202 are possible.

FIG. 2 further illustrates a brain activity signal 206, which comprises neural oscillations. As can be seen in FIG. 2, the brain activity signal 206 comprises frequency content in a large range of frequencies. However, the frequency of interest may be extracted from the brain activity signal 206 with phase information being extracted, as will be further described below.

FIG. 2 further illustrates a stimulation signal 208 which is paused during a control interval 210. Thus, the stimulation signal 208 does not interfere with determination of the phase relation between the HF synchro signal 202 and the neural oscillations of the brain activity signal 206.

It should be realized that a measurement signal, which may be acquired by the measurement unit 130, will initially comprise the response to the HF synchro signal 202 and the brain activity signal 206. Thus, the signals 202 and 206 illustrated in FIG. 2 are actually superposed on each other in the measurement signal.

The extracted phase information of the frequency of interest of the neural oscillations may be compared to the instants of the spikes 204 of the HF synchro signal 202. Thus, a phase difference may be determined corresponding to the phase of the frequency of interest of the neural oscillations at an instant corresponding to the spikes 204 in the HF synchro signal 202. Since the spikes 204 are periodically provided with the same frequency as the frequency of interest, the same phase difference will or should apply at each of the instants of the spikes 204. The phase difference may be determined based on an average of the phase difference over a plurality of spikes 204.

Further, a desired phase relation between the stimulation signal and the frequency of interest of the neural oscillations may be set. This desired phase relation may be set in relation to a desired interference of the stimulation signal with the neural oscillations. For example, the desired phase relation may define that the stimulation signal is to be synchronized (i.e. a phase difference of 0°) with the neural oscillations, such that a constructive interference is achieved. The desired phase relation may define that the stimulation signal is to be set to a phase offset of 180° to the neural oscillations, such that a destructive interference is achieved. It should however be realized that the desired phase relation may defined in any other manner for achieving any phase relation between the stimulation signal and the neural oscillations.

The determined phase difference between the phase of the neural oscillations and the instants of the HF synchro signal 202 may thus be compared to the desired phase relation. The phase of the stimulation signal 208 may thus be set in relation to the instants of spikes 204 in the HF synchro signal 202 such that a desired phase relation may be achieved between the phase of the neural oscillations and the phase of the stimulation signal 208. Since the determined phase difference between the phase of the neural oscillations and the instants of the HF synchro signal 202 can be considered to be fixed, the stimulation signal 208 needs only be related to the instants of spikes 204 in the HF synchro signal 202 such that the desired phase relation to the neural oscillations is achieved. Hence, based on a deviation between the determined phase difference and a desired phase relation, an adjustment of phase of the stimulation signal 208 may be determined. For instance, if the phase difference between the phase of the neural oscillations and the instants of the HF synchro signal 202 is determined to be 20° and the desired phase relation between the stimulation signal 208 and the neural oscillations is 0°, an adjustment of the phase of the stimulation signal 208 may be determined to be −20°, such that the stimulation signal 208 may be output by the stimulation generator 120 with a phase of −20° corresponding to the instants of the spikes 204 of the HF synchro signal 202.

However, according to an embodiment, the stimulation signal 208 may always be output to be synchronized with the HF synchro signal 202. This implies that a phase of the stimulation signal 208 should be 0° at the instant of the spikes 204 of the HF synchro signal 202. Thus, instead of determining a phase offset of the stimulation signal 208 to the HF synchro signal 202, an adjustment of timing of the spikes 204 of the HF synchro signal 202 may be performed. This implies that adjustment of the phase determined based on comparing the phase difference between the phase of the neural oscillations and the instants of the HF synchro signal 202 to the desired phase relation may be used to adjust the timing of the spikes 204 of the HF synchro signal 202. When the stimulation signal 208 is then output in synchronization with the spikes 204 of the HF synchro signal 202, the stimulation signal 208 will be output with the desired phase relation to the neural oscillations.

As shown in FIG. 2, the stimulation signal 208 is output after the control interval 210 with the stimulation signal 208 being synchronized (phase=0°) with the spikes 204 of the HF synchro signal 202.

The frequency of interest may be set in relation to a desired neural oscillation to be strengthened or suppressed. This frequency may be set in advance. For instance, the frequency of interest may be set such that the stimulation signal 208 is to be used for strengthening alpha waves in the brain of the subject. In this regard, the frequency of interest may be set to any frequency within the range of alpha waves, such as a frequency of 10 Hz. The frequency of interest may be set independently of actual brain activity in the subject.

However, according to an alternative, an initial calibration may be performed. Thus, the measurement unit 130 may be used for acquiring an initial calibration measurement signal from the brain of the subject. The initial calibration measurement signal may represent the brain activity comprising neural oscillations of the subject to which brain stimulation is to be provided.

The control unit 110 may then be configured to receive the initial calibration measurement signal. The control unit 110 may further analyze the calibration measurement signal in order to determine a personalized frequency of interest. This personalized frequency of interest may for instance be a peak frequency (frequency having highest amplitude in the calibration measurement signal) in a desired range of frequencies, such that a peak frequency of alpha waves for the subject may be selected as the frequency of interest. This may allow the stimulation signal 208 to be provided to interfere with the peak frequency, which may be used e.g. for strengthening a strongest frequency among the alpha waves in the subject. It should however be realized that the personalized frequency of interest may be determined in other ways and may not necessarily correspond to a peak frequency of the neural oscillations.

The HF synchro signal 202 may be set such that the periodicity of the spikes 204 correspond to the frequency of interest. The periodicity of the spikes 204 may thus be adjusted in relation to the personalized frequency.

A period between the spikes 204 may equal a period corresponding to the frequency of interest. However, it should be realized that the period between the spikes 204 need not equal an entire period corresponding to the frequency of interest. Rather, the period between the spikes 204 may be provided such that several spikes 204 have a common phase difference to the frequency of interest. This may be achieved by the period between the spikes 204 corresponding to an integer number of periods of the frequency of interest. For instance, a period between the spikes 204 may equal two periods of a wave of the frequency of interest. Alternatively, an integer number, larger than one, of periods between the spikes 204 may equal one period of a wave of the frequency of interest. As yet another alternative, an integer number, larger than one, of periods between the spikes 204 may equal another integer number, larger than one, of periods of the wave of the frequency of interest.

Figure 3:
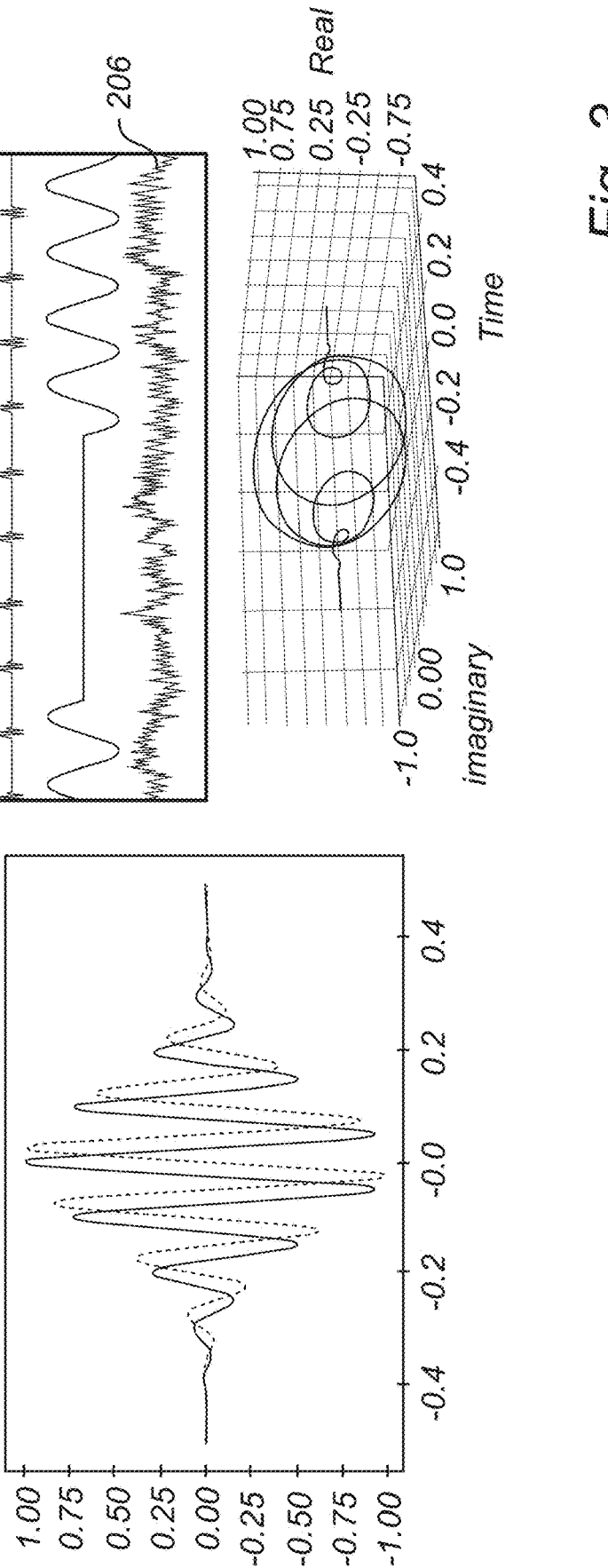
FIG. 3 shows graphs of a complex Morlet wavelet used for analysis of the brain activity signal, which is also schematically illustrated.

Referring now to FIG. 3, determining the phase of the neural oscillations will be described.

As shown in FIG. 3, the phase of the neural oscillations may be determined using a wavelet transform. In the graph on left side of FIG. 3, a real part of a complex Morlet wavelet is shown, whereas in bottom graph on right side of FIG. 3, imaginary and real parts of the complex Morlet wavelet are shown. The complex Morlet wavelet is a combination of cosine and imaginary cosine waves. The complex Morlet wavelet may be set in relation to the frequency of interest. The complex Morlet wavelet shown in FIG. 3 forms a 10 Hz complex Morlet wavelet.

A wavelet transform may be applied to the measurement signal representing brain activity 206 using the complex Morlet wavelet. This implies that the complex Morlet wavelet is convolved over the entire signal representing brain activity 206 shown in top graph on right side of FIG. 3. Although FIG. 3 shows the complex Morlet wavelet in a 1 second window, it should be realized that other lengths of this window, longer or shorter, may be used.

After the wavelet transform has been applied, a time series of imaginary numbers is output, wherein the time series includes amplitude and phase at each time point for the frequency of interest.

Hence, the phase at each time point may be determined. The determined phase at the time points corresponding to the spikes 204 of the HF synchro signal 202 may then be used as a phase difference between the neural oscillations and the spikes 204 of the HF synchro signal 202.

It should be realized that alternative transforms may be used for determining the phase of the neural oscillations. For instance, a Hilbert transform may be used instead.

Referring now to FIG. 4, determining a timing of the spikes 204 of the HF synchro signal 202 will be described.

The response of the HF synchro signal 202 may be extracted from the measurement signal, e.g. by applying a narrow filter adapted to the high frequency used in the HF synchro signal 202. For instance, the spikes 204 of the HF synchro signal 202 may be applied using a frequency of 100 Hz. Since the frequency content of the HF synchro signal 202 is known, the filter may be easily adapted to extract the HF synchro signal 202 from the measurement signal.

Then, the HF synchro signal 202 may be analyzed in order to identify the spikes 204 of the HF synchro signal 202. Any suitable feature in the HF synchro signal 202 may be used in order to identify the spikes 204. For example, as indicated in top graph of FIG. 4, the amplitude of the HF synchro signal 202 may be analyzed in order to determine local peak amplitudes. Each peak amplitude may then be considered to correspond to a time point of a spike 204 in the HF synchro signal 202.

Then, phase information of the frequency of interest of the neural oscillations may be compared to timing of the spikes 204 in the HF synchro signal. In the bottom graph of FIG. 4, a representation of the frequency of interest of the neural oscillations (dashed line) is illustrated together with a representation of the amplitude of the HF synchro signal 202 (solid line). The time points of the peak amplitude of the HF synchro signal 202 are indicated as well as the time points corresponding to peaks in the neural oscillations.

Hence, based on the phase information of the neural oscillations and the timing of the spikes 204 of the HF synchro signal 202, the phase difference between the phase of the neural oscillations and the instants of the HF synchro signal 202 may be determined.

The determination of the phase difference between the phase of the neural oscillations and the instants of the HF synchro signal 202 may be performed for time windows corresponding to a control interval 210. Thus, only the signals during such time window need to be analyzed.

The time window may be relatively short, such as less than 10 seconds or less than 3 seconds. The phase of the stimulation signal may be updated in order to adapt to changes in phase of the neural oscillations. Having a short time window allows stimulation with an updated phase of the stimulation signal 208 to be resumed quickly after an updating of the phase of the stimulation signal 208, such that the stimulation signal 208 may be updated in real-time during a session of providing a stimulation signal 208 to the subject.

Using the time window, the measurement signal may still comprise a plurality of periods of the frequency of interest. This allows a phase difference to be determined at a plurality of points in time. These phase differences may be used for determining an average phase difference, which may be used in controlling phase of the stimulation signal 208. Hence, a robust determination of the phase difference may be used.

Referring now to FIG. 5, a method for controlling a stimulation signal for brain stimulation will be briefly summarized. The method may be implemented in the control unit 110 which may provide control signals for causing actions to be taken in other components of the system 100.

The method comprises transmitting 302 a trigger signal for triggering the stimulation generator 120 to output the HF synchro signal 202. Thus, output of the HF synchro signal is initiated, which allows the phase relation between the frequency of interest of the neural oscillations and the spikes 204 of the HF synchro signal 202 to be determined.

The method further comprises receiving 304 a measurement signal representing brain activity 206 comprising neural oscillations and a response to the HF synchro signal 202. The measurement signal may comprise the response to the HF synchro signal 202 superposed on the brain activity 206. The measurement signal may be analyzed, possibly including filtering the measurement signal to separate the HF synchro signal 202 from the brain activity 206. Based on analysis of the measurement signal, timing of the spikes 204 of the HF synchro signal 202 and the phase of the frequency of interest of the neural oscillations at different time points may be determined. Further, a phase difference between the neural oscillations and the spikes 204 of the HF synchro signal 202 may then be determined.

The method further comprises determining 306 adjustment of a phase of the stimulation signal 208 based on the determined phase difference between the neural oscillations and the spikes 204 of the HF synchro signal. The phase difference may be compared to a desired phase relation between the stimulation signal 208 and the neural oscillations and based on such comparison the adjustment of the phase of the stimulation signal 208 to be applied may be determined.

The method further comprises transmitting 308 a phase information signal for providing information of an adjusted phase of the stimulation signal 208 to be used by the stimulation generator 120. Thus, the adjustment may be provided to the stimulation generator 120 such that the phase of the stimulation signal 208 may be set in relation to the spikes 204 of the HF synchro signal 202 and/or the timing of the spikes 204 of the HF synchro signal 202 may be adjusted such that the stimulation signal 208 can be output with a desired phase relation to the neural oscillations in the brain activity 206.

The HF synchro signal 202 uses a frequency which will typically not interfere with frequency content of the brain activity. This implies that the HF synchro signal 202 may be easily identified in the measurement signal and will not be hidden by other signals. Thus, the stimulation generator 120 may be controlled to output a low amplitude of the HF synchro signal 202 while still allowing the HF synchro signal 202 to be properly detected.

This implies that it may be ensured that the HF synchro signal 202 will not affect the brain of the subject. Further, output of the HF synchro signal 202 may consume a low amount of power in the stimulation generator 120. The amplitude of the HF synchro signal 202 may be controlled to be lower than the amplitude of the stimulation signal 208, such as lower than 50% of the amplitude of the stimulation signal 208.

Figure 6:
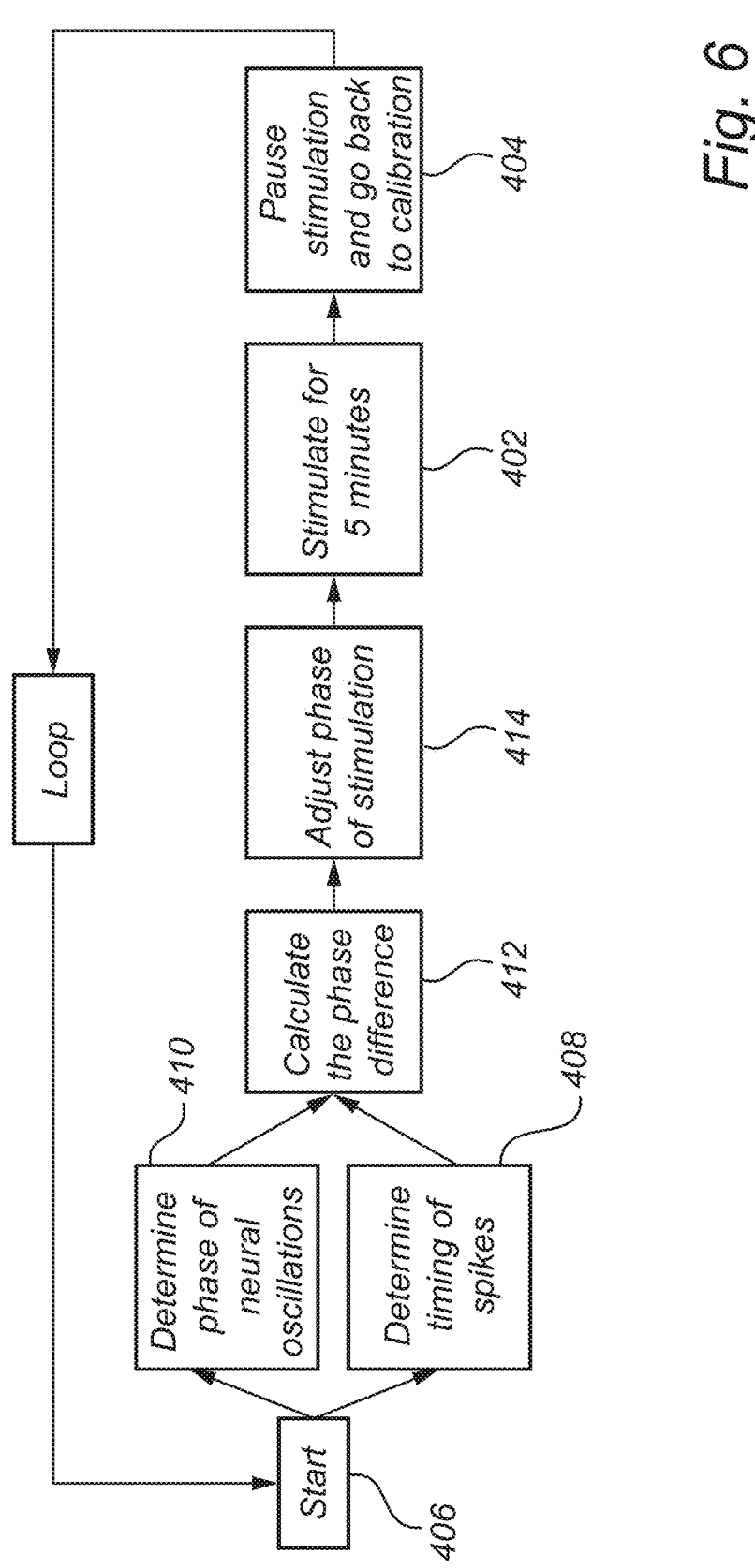
FIG. 6 is a flow chart of a method for updating a phase of the synchronization signal according to an embodiment.

Referring now to FIG. 6, periodical updating of the phase of the stimulation signal 208 will be described. Thus, a calibration may be performed periodically to ensure that the desired phase relation between the stimulation signal 208 is maintained.

A determined phase of the stimulation signal 208 may be used for a period of time during which it may be assumed that there is a relatively low drift in phase of the neural oscillations. For instance, the stimulation signal 208 may be used with a determined phase for stimulation 402 during a period of 5 minutes.

When it is time to perform an updating of the phase of the stimulation signal, the control unit 110 may transmit a pause signal for pausing 404 output of the stimulation signal.

Thus, an updated calibration of the phase relation between the stimulation signal 208 and the neural oscillations may be started 406. The calibration may be performed in similar manner as described above, involving receiving an updated measurement signal, determining 408 timing of the spikes 204 of the HF synchro signal 202 and determining 410 the phase of the frequency of interest of the neural oscillations at different time points. Then, a phase difference between the neural oscillations and the spikes 204 of the HF synchro signal 202 may be determined 412.

Based on the phase difference, an updated adjustment of a phase of the stimulation signal 208 may be determined 414 and an updated phase information signal providing information of the updated adjustment of the phase of the stimulation signal 208 may be transmitted to the stimulation generator 120.

Then, stimulation may be resumed to again provide stimulation 402 using the stimulation signal 208 with the updated adjustment of the phase during a period of 5 minutes.

Figure 7A:
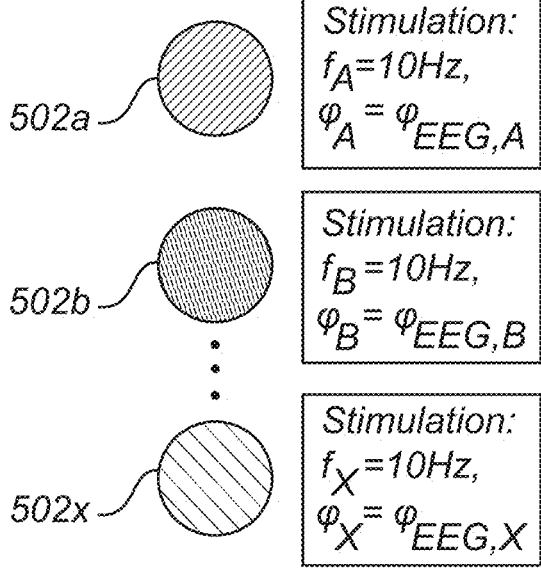
FIGS. 7a-7b are schematic views illustrating a system comprising a plurality of stimulation electrodes according to different embodiments.
Figure 7B:
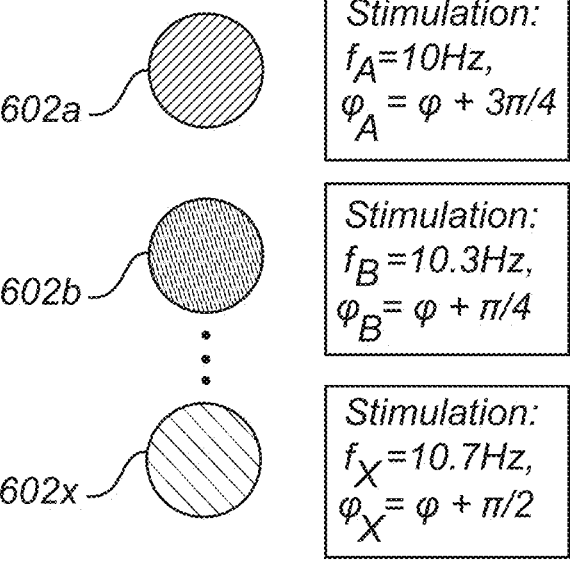

Referring now to FIGS. 7a-7b, the system 100 may further comprise a plurality of stimulation electrodes 502, 602. The system 100 may be configured to provide a plurality of stimulation signals 208 through the plurality of stimulation electrodes 502, 602.

The plurality of stimulation signals 208 may be used for independent stimulation at a plurality of locations or may be used for combined multi-electrode stimulation.

In one embodiment, illustrated in FIG. 7a, independent stimulation is provided at a plurality of locations. At each location, stimulation electrodes 502 and measurement electrodes 104 are used close to the location. The stimulation signal 208 is controlled in relation to the phase difference determined based on a locally recorded measurement signal. This would enable localized stimulation with a desired phase relation to the locally occurring brain activity at different brain regions (i.e., electrode locations).

Thus, a stimulation electrode 502a may be provided with a stimulation signal 208 that is determined based on a measured phase of the neural oscillations at its location, $\varphi$EEG,A. Thus, the phase of the stimulation signal 208 at the stimulation electrode 502a may be set as $\varphi$A=$\varphi$EEG,A. Similarly, a stimulation electrode 502b may be provided with a stimulation signal 208 that is determined based on a measured phase of the neural oscillations at its location, $\varphi$EEG,B. Thus, the phase of the stimulation signal 208 at the stimulation electrode 502b may be set as $\varphi$B=$\varphi$EEG,B. This may be true for each of the stimulation signals 208 associated with each of the stimulation electrodes 502a-502x. It should be realized that the stimulation signals 208 need not necessarily be synchronized with the neural oscillations. Instead, a phase offset may be used. Also, it should be realized that different offsets may be used for different locations.

Each of the stimulation signals 208 may have a same frequency, illustrated in FIG. 7a as being 10 Hz. Alternatively, the stimulation signals 208 may have different frequencies. Since each of the stimulation signals 208 is individually controlled, the stimulation signals 208 may be provided by different stimulation generators and it is not necessary to ensure any synchronization between different stimulation signals 208.

In another embodiment, illustrated in FIG. 7b, combined stimulation may be provided based on the plurality of stimulation electrodes 602. The brain activity may be measured at each of the locations of the stimulation electrodes 602 or at least in multiple locations. The phase of each of the stimulation signals 208 may be set in relation to a combination of the phases (e.g. an average phase) at the multiple locations.

Hence, the phases of each of the stimulation signals 208 may be related to each other. This would require a centralized synchronization signal across all the stimulation electrodes 602. Such centralized synchronization signal may be achieved using a common signal generator for all the stimulation electrodes 602 for providing the synchronization signal.

Each of the stimulation signals 208 may be provided with different frequencies and/or different phase offsets to the combined phase of the neural oscillations. Thus, the system 100 may be configured to control a relative phase and/or a relative frequency of the plurality of stimulation signals 208.

The use of different frequencies and/or phase offsets for the plurality of stimulation signals 208 may facilitate brain stimulation that can enable strengthening or weakening network interaction within the brain, considering both frequency and phase.

Thus, a stimulation electrode 602a may be provided with a stimulation signal 208 that has a particular phase relation to the average phase $\varphi$ of the neural oscillations. Thus, the phase of the stimulation signal 208 at the stimulation electrode 602a may be set as $\varphi A=\varphi+3\pi/4$. Similarly, a stimulation electrode 602b may be provided with a stimulation signal 208 that has another particular phase relation to the average phase $\varphi$ of the neural oscillations. Thus, the phase of the stimulation signal 208 at the stimulation electrode 602b may be set as $\varphi$B=$\varphi+\pi/4$. Thus, different phase relations may be used for the stimulation signals 208 for each of the stimulation electrodes 602a-602x with the phase of the stimulation signal 208 at the stimulation electrode 602x being set as $\varphi$x=$\varphi+\pi/2$.

Each of the stimulation signals 208 may have a same frequency. Alternatively, the stimulation signals 208 may have different frequencies, such as the stimulation signal 208 associated with the stimulation electrode 602a having a frequency of $f_A$=10 Hz, the stimulation signal 208 associated with the stimulation electrode 602b having a frequency of $f_B$=10.3 Hz, and the stimulation signal 208 associated with the stimulation electrode 602x having a frequency of fx=10.7 Hz.

It should be realized that the phase offsets and frequencies indicated are mere examples and different relations between phases and/or frequencies for different stimulation signals 208 may be used.

Further, it should be realized that control of phase and/or frequency of the stimulation signals 208 associated with a plurality of electrodes 502, 602 may be performed in many other ways.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A method for controlling a stimulation signal for brain stimulation, said method comprising:

transmit a trigger signal for triggering a stimulation generator to output a high frequency synchronization signal exhibiting periodical modifications to synchronize with brain activity without affecting brain activity;

receive a measurement signal representing brain activity comprising neural oscillations and a response to the high frequency synchronization signal;

determine adjustment of a phase of the stimulation signal based on a phase difference between the neural oscillations and the modifications of the high frequency synchronization signal; and transmit a phase information signal for providing information of an adjusted phase of the stimulation signal to be used by the stimulation generator.

2. The method according to claim 1, further comprising updating adjustment of a phase of the stimulation signal, wherein said updating comprises:

transmit a pause signal for pausing the stimulation generator from outputting the stimulation signal;

receive an updated measurement signal representing the brain activity comprising neural oscillations and the response to the high frequency synchronization signal;

determine an updated adjustment of a phase of the stimulation signal based on the phase difference between the neural oscillations and the modifications of the high frequency synchronization signal;

transmit an updated phase information signal for providing information of an updated adjusted phase of the stimulation signal to be used by the stimulation generator.

3. The method according to claim 2, wherein a time window between the pause signal and the updated phase information signal is less than 10 seconds.

4. The method according to claim 1, wherein the stimulation generator is controlled to output the high frequency synchronization signal with a lower amplitude than the stimulation signal.

5. The method according to claim 1, wherein the stimulation generator is triggered to output the high frequency synchronization signal with periodical modifications, wherein a periodicity of the modifications is an integer number of a frequency of the neural oscillations.

6. The method according to claim 5, further comprising receiving an initial calibration measurement signal representing the brain activity comprising neural oscillations, determining a personalized frequency of the neural oscillations, and controlling the stimulation generator to output the high frequency synchronization signal with the periodicity of the modifications being an integer number of the personalized frequency of the neural oscillations.

7. The method according to claim 1, wherein determining adjustment of the phase of the stimulation signal comprises determining a phase of the neural oscillations using a wavelet or Hilbert transform.

8. The method according to claim 1, wherein determining adjustment of the phase of the stimulation signal comprises determining a timing of the modifications of the high frequency synchronization signal based on detecting a peak amplitude of the modifications.

9. A non-transitory computer program product comprising computer-readable instructions such that when executed on a processing unit the computer-readable instructions will cause the processing unit to perform the method according to claim 1.

10. A control unit for controlling a stimulation signal for brain stimulation, wherein the control unit is configured to perform the method according to claim 1.

11. A system for providing a stimulation signal for brain stimulation, wherein the system comprises:
the control unit according to claim 10, and
a stimulation generator, which is configured to receive the trigger signal and the phase information signal from the control unit and is configured to generate and output the high frequency synchronization signal exhibiting periodical modifications and the stimulation signal.

12. The system according to claim 11, wherein the stimulation generator is configured to provide a synchronized output of the stimulation signal with the periodical modifications of the high frequency synchronization signal, and wherein the stimulation generator is configured to adjust a timing of the periodical modifications for adjusting the phase of the stimulation signal.

13. The system according to claim 11, wherein the stimulation generator is configured to output the stimulation signal to provide transcranial alternating current stimulation.

14. The system according to claim 11, wherein the system further comprises a plurality of stimulation electrodes for providing a plurality of stimulation signals to the brain through the plurality of stimulation electrodes.

15. The system according to claim 14, wherein the system is configured to control a relative phase and/or a relative frequency of the plurality of stimulation signals.

* * * * *